United States Patent [19]

Bohnen

[11] 4,434,165

[45] Feb. 28, 1984

[54] FUNGICIDAL COMPOSITIONS

[75] Inventor: Klaus Bohnen, Dielsdorf, Switzerland

[73] Assignee: Hoffmann-La Roche Inc., Nutley, N.J.

[21] Appl. No.: 304,484

[22] Filed: Sep. 22, 1981

[30] Foreign Application Priority Data

Sep. 30, 1980 [CH] Switzerland .................. 7311/80
Jul. 14, 1981 [CH] Switzerland .................. 4611/81

[51] Int. Cl.$^3$ .......................................... A01N 43/84
[52] U.S. Cl. .................................................. 424/248.4
[58] Field of Search ..................................... 424/248.4

[56] References Cited

U.S. PATENT DOCUMENTS

| | | | |
|---|---|---|---|
| 4,079,143 | 3/1978 | Balasubramanyan et al. | 424/269 |
| 4,202,894 | 5/1980 | Pfiffner | 424/248.4 |
| 4,205,075 | 5/1980 | Baldwin et al. | 424/269 |
| 4,241,058 | 12/1980 | Pfiffner | 424/248.4 |
| 4,243,405 | 1/1981 | Balasubramanyan et al. | 424/245 |

FOREIGN PATENT DOCUMENTS 1579688 11/1980 United Kingdom .

*Primary Examiner*—Allen J. Robinson

*Attorney, Agent, or Firm*—Jon S. Saxe; George M. Gould; John J. Maitner

[57] ABSTRACT

Fungicidal compositions which contains at least one compound of the formula

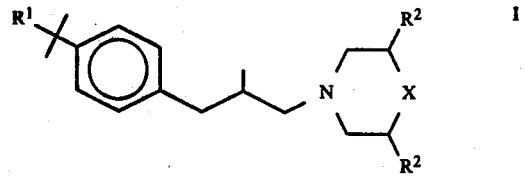

wherein $R^1$, $R^2$ and X are as hereinafter set forth, and at least one compound of the formula

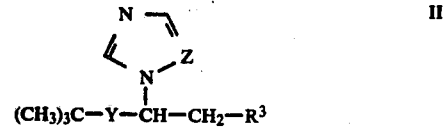

wherein $R^3$, Y and Z are as hereinafter set forth, and, where required, formulation adjuvants, processes for their preparation and methods for using the compositions for the control of plant fungi are disclosed.

3 Claims, No Drawings

FUNGICIDAL COMPOSITIONS

BRIEF SUMMARY OF THE INVENTION

The invention relates to fungicidal compositions comprising at least one compound of the formula

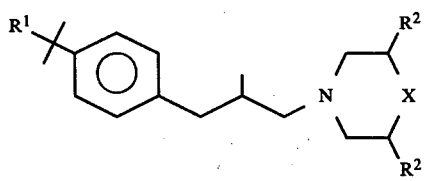

wherein $R^1$, $R^2$ and X are as hereinafter described and at least one compound of the formula

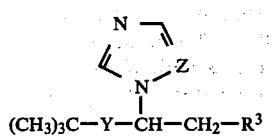

wherein $R^3$, Y and Z are as hereinafter described and, where required, formulation adjuvants.

In another aspect, the invention relates to processes for preparing the fungicidal compositions and methods for controlling plant fungi.

DETAILED DESCRIPTION OF THE INVENTION

A multiplicity of fungicides are used in agriculture to control crop diseases which reduce yield and quality. The compound 1-tert.butyl-2-(1,2,4-triazol-1-yl)-2-(o,p-dichlorobenzyl)-ethanol, also known under the name "Diclobutrazol", as well as compounds closely related thereto are used to control damaging crop leaf diseases which are caused by Erysiphe, Puccinia, Rhynchosporium and Helminthosporium species of fungi. However, these compounds have the disadvantage that in effective dosages they can exhibit an undesirable growth regulatory activity on certain types of crops. This occurs especially with the early application of such compounds and manifests itself in an inhibition of the plant growth as a consequence of internodal reductions.

It has been found that this disadvantage can be reduced or even eliminated by the simultaneous application of one or more of the compounds mentioned above and one or more phenylalkylmorpholine or phenylalkylpiperidine derivatives of formula I, as defined hereinafter, which also possess fungicidal properties. Further, it has been found that in the combination of the aforementioned components the difference between the effective dosage and the toxic dosage is greater and accordingly safer in practice than is the case when the phenylalkymorpholine or phenylalkylpiperidine derivatives of formula I are used alone.

It is an object of the present invention to reduce or eliminate the undesirable growth regulatory activity of "Diclobutrazol" or compounds closely related thereto as well as to improve the chemotherapeutic index, i.e. to increase the aforementioned difference when using phenylalkylmorpholine or phenylalkylpiperidine derivatives.

The present invention is directed to fungicidal compositions, which comprise at least one compound of the formula

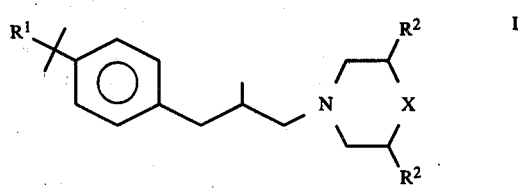

wherein $R^1$ is lower alkyl or phenyl, and either X is oxygen and $R^2$ is methyl, or X is methylene and $R^2$ is hydrogen or methyl, and at least one compound of the formula

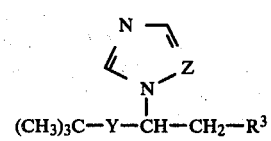

wherein Y signifies a group of formula (a) or (b)

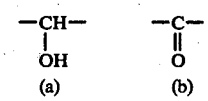

Z is CH or N, and $R^3$ is p-chlorophenyl or o,p-dichlorophenyl, and, where required, formulation adjuvants.

As used herein, the term "lower alkyl" denotes a hydrocarbon group containing from 1 to 4 carbon atoms.

It has furthermore been found that the use of the compositions of this invention unexpectedly decrease the amount of active ingredient combination to be applied. From this it can be concluded that the individual active ingredients of the combination support each other mutually and advantageously in their activity, i.e. a synergism occurs.

The use of the fungicidal compositions of this invention in agriculture results inter alia in the following advantages:

Reduction of the amount of active substance required for the effective control of fungal diseases.

Less contamination of harvested crops, soil and water by the application of smaller amounts of active substance per hectare and treatment.

Elimination of the disadvantageous growth regulatory effect which can influence the plant growth by internodal reduction when the compounds of formula II are used alone.

Substantial improvement of the plant tolerance vis-a-vis that when the individual ingredients of the combination are used alone.

In the control of cereal diseases, improvement of the chemotherapeutic index.

Preferred compounds of formula I for the fungicidal compositions of this invention are those in which X is oxygen and $R^2$ is methyl, as well as those in which $R^1$ is methyl, ethyl or phenyl. Especially preferred compounds of formula I are 4-[3-(p-tert.butyl-phenyl)-2-methyl-propyl]-2,6-dimethyl-morpholine and 1-[3-(p- tert.butyl-phenyl)-2-methyl-propyl]-piperidine, particularly the cis isomer of the former compound.

An especially preferred compound of Formula II is 1-tert.-butyl-2-(1,2,4-triazol-1-yl)-2-(o,p-dichlorobenzyl)-ethanol.

The compound of formula I and II are known and can be prepared according to known methods. The compounds of formula I are prepared according to processes described in German Offenlegungsschrift No. 2 752 135 and the compound of formula II are prepared according to processes described in Belgian Specification No. 857 836 and German Offenlegungsschrift No. 2 638 470.

The compositions of this invention are effective against a wide variety of fungi on plants and are useful for the control of fungi in agriculture and in horticulture. The compositions are especially suitable for the preventative and curative treatment of powdery mildew fungi such as, for example, Erysiphe graminis on types of cereal and organisms which cause rust diseases such as, for example, those of the genera Puccinia, Uromyces, Phragmidium and Hemileia.

Furthermore, the compositions of the present invention also exhibit a pronounced fungicidal activity against phytopathogenic fungi such as, for example, those of the following genera: Ustilago, Cercospora, Rhynchosporium, Tilletia, Helminthosporium, Coniophora, Lenzites, Thielaviopsis, Fusarium, Pyricularia and Penicillium.

The compositions of the present invention can contain in addition to the compounds of formula I and II, formulation adjuvants, such as solid carrier materials, solvents and dispersion media, tensides (wetting and emulsifying agents), dispersing agents (without tenside action) and/or stabilizers.

The compounds of formula I and II can be used with these and other adjuvants to prepare fungicidal formulations in the form of dusts, powders, granulates, solutions, emulsions, suspensions, emulsifiable concentrates, pastes and the like.

The compounds of formula I and II are in general insoluble in water and can be formulated according to methods which are usual for water-insoluble compounds, if necessary using the respective formulation adjuvant. The fungicidal compositions of this invention can be prepared by mixing at least one compound of formula I with at least one compound of formula II and, where required, with formulation adjuvants.

Examples of solid carrier materials include mineral substances such as, for example, chalk, dolomite, limestone and silicic acid and salts thereof, e.g. siliceous earth, kaolin, bentonite, talc, and the like; organic substances such as, for example, cellulose, starch, urea and synthetic resins; and fertilizers such as, for example, phosphates and nitrates. Such carrier materials can be present as powders or as granulates.

Examples of solvents or dispersion media include alcohols, ketones, esters, aliphatic and aromatic hydrocarbons and chlorinated aliphatic and aromatic hydrocarbons, and water. Preferably such organic solvents or dispersion media have flash points of at least 30° C. and boiling points of at least 50° C.

Examples of tensides (wetting and emulsifying agents) include non-ionic compounds such as condensation products of fatty acids, fatty alcohols or fatty-substituted phenols with ethylene oxide; fatty acid esters and fatty acid ethers of sugars or polyvalent alcohols; the products which are obtained from sugars of polyvalent alcohols by condensation with ethylene oxide; block polymers of ethylene oxide and propylene oxide; or alkyldimethylamine oxides.

Examples of tensides are anionic compounds include soaps; fatty sulphate esters (e.g. dodecyl sodium sulphate, octadecyl sodium sulphate and cetyl sodium sulphate); fatty-aromatic sulphonates (e.g. alkylbenzene sulphonates such as calcium dodecylbenzene sulphonate, and butylnaphthalene sulphonate); and more complex fatty sulphonates, for example the amide condensation products of oleic acid and N-methyltaurine and the sodium sulphonate of dioctyl succinate.

Examples of tensides which are cationic compounds include alkyldimethylbenzylammonium chlorides, dialkyldimethylammonium chlorides, alkyltrimethylammonium chlorides and ethoxylated quaternary ammonium chlorides.

Examples of dispersing agents without tenside action include sodium and ammonium salts of lignin sulphonic acid, sodium salts of maleic acid anhydride/diisobutylene copolymers and sodium and ammonium salts of polycondensation products of naphthalene and formaldehyde.

As dispersing agents, which are especially suitable as thickening agents or anti-settling agents, there can be used, for example, methylcellulose, carboxymethylcellulose, hydroxycellulose, polyvinyl alcohol, alginates, caseinates and blood albumin.

Examples of suitable stabilizers are acid-binding agents, for example epichlorohydrin, phenyl glycidyl ether, soya epoxides, and the like; antioxidants, for example, gallic acid esters, butylhydroxytoluene, and the like; UV-absorbers, for example, substituted benzophenones, diphenylacrylonitrile acid esters, cinnamic acid esters and the like; and deactivators, for example, salts of ethylenediaminotetraacetic acid, polyglycols, and the like.

The fungicidal compositions of this invention can contain solid carrier materials in a concentration of between 1 and 99.9%, the solvents or dispersion media are present in a concentration of between 1 and 99.9%, the tensides are present in a concentration of between 1 and 20%, the dispersing agents are present in a concentration of between 1 and 20%, the dispersing agents as thickening agents or anti-settling agents are present in a concentration of between 0.1 and 5% and the stabilizers are present in a concentration range between 0.1 and 5%; these percentages refer to the total weight of the composition.

The fungicidal compositions of this invention can be prepared by known procedures; for example, mixing the respective active ingredients with solid carrier materials, dissolving or suspending in suitable solvents or dispersion media, if necessary using tensides as wetting or emulsifying agents, or diluting pre-prepared emulsifiable concentrates with solvents or dispersion media, and the like.

For the preparation of pulverous preparations, the active ingredients of formula I and II can be mixed with solid carrier materials, for example by grinding them together, or the solid carrier materials can be impregnated with a solution or dispersion of the active ingredients and the solvent or dispersion medium is then removed by evaporation, heating or by filtration under reduced pressure. Such pulverulent fungicidal compositions can be rendered easily wettable with water by adding tensides and/or dispersing agents so that they can be used in the form of aqueous suspensions, e.g. as spray compositions.

The compounds of formula I and II can also be mixed with a tenside and a solid carrier material to form a wettable powder which is dispersible in water, or they can be mixed with a solid pre-granulated carrier material to form a product in the form of a granulate.

To prepare emulsifiable concentrated, the active ingredients, i.e. the compounds of formula I and II, can be mixed with an emulsifying agent or dissolved in a water-immisible solvent such as, for example, an alicyclic ketone, containing an emulsifier. Ready-for-use emulsions are prepared by dilution of such concentrates with water. These concentrates can contain from about 5 percent to 95 percent by weight, and, preferably, from about 25 percent to about 75 percent by weight of the active ingredients, i.e. compounds of formula I and II.

The fungicidal composition can also be present in the form of a pressurized pack, a solvent conveniently being used in addition to the propellant, which is suitably a liquified polyhalogenated alkane such as dichlorodifluoromethane.

The fungicidal compositions of this invention can contain, in addition to the compounds of formula I and II, other active ingredients (e.g. other fungicidal agents, insecticidal agents, acaricidal agents, bactericides, herbicides, plant growth regulating agents, fertilizers and the like). Such combination compositions are useful either for broadening the spectrum of activity or for specifically influencing the plant growth. Examples of some known active ingredients active are O,O-dimethyl-S-(1,2-dicarbethoxyethyl)-dithiophosphate, O,O-diethyl-O-(p-nitrophenyl)-thiophosphate, ψ-hexachlorocyclohexane, 2,2-bis-(p-ethylphenyl)-1,1-dichloroethane, p-chloro-benzyl-p-chlorophenylsulphide, 2,2-bis-(p-chlorophenyl)-1,1,1-trichloroethanol, manganese- and zinc-ethylenebisdithiocarbonate, N-trichloromethyl-thiotetrahydrophthalimide, 1-(butylcarbamoyl)-2-benzimidazolecarbamate, 2,4,5,6-tetrachloro-1,3-benzenedicarbonitrile and 3a,4,7,7a-tetrahydro-N(1,1,2,2-tetrachloro-ethanesulphenyl)phthalimide.

The fungicidal compositions of this invention generally contain from about 0.01 percent to about 90 percent by weight of the combination of the compounds of formula I and II and, conveniently, formulation adjuvants. They can be present, for example, in the form which is suitable for storage and transport. In such formulations (e.g. emulsifiable concentrates) the active ingredient concentration is normally in the higher range, preferably from about 25 percent to 75 percent by weight, especially from about 40 percent to about 60 percent by weight. These formulations can subsequently be diluted, for example with the same or different formulation adjuvants, to afford active ingredient concentrations which are suitable for practical use, i.e. preferably from about 0.01 percent to about 0.5 percent by weight. The active ingredient concentrations can, however also be smaller or greater. In the case of granulates etc, the concentrations generally are from about 3 percent to about 10 percent by weight.

The compounds of formula I and II are preferably mixed in a ratio of about 2:1 to about 10:1, especially from about 3:1 to about 9:1.

The use of the fungicidal compositions of this invention can be carried out according to application methods which are usual in plant protection such as sprinkling, spraying, dusting, pouring or scattering. The method of this invention for the control of plant fungi comprises treating the plants to be protected with an effective amount of an active ingredient combination of this invention. Pulverous preparations can, for example, be applied to the plants to be protected as dusting compositions with the aid of usual dusting implements. Aqueous suspensions can be used, for example, as spray compositions.

In their various fields of use the compositions of this invention can be employed in different amounts. For the treatment of plants for the control of fungi there are conveniently used 250–600 g, especially 300–400 g, of an active ingredient combination of this invention per hectare and treatment.

The following Examples illustrate the invention in more detail.

EXAMPLE 1

This Example illustrates the preparation of a spray powder

|  | Weight percent |
|---|---|
| Active ingredient of formula I, e.g. 4-[3-(p-tert.butyl-phenyl)-2-methyl-propyl]-2,6-dimethyl-morpholine or 1-[3-(p-tert.butyl-phenyl)-2-methyl-propyl]-piperidine | 36.0 |
| Active ingredient of formula II, e.g. 1-tert.butyl-2-(1,2,4-triazol-1-yl)-2-(o,p-dichlorobenzyl)-ethanol | 4.0 |
| Hydrated silicic acid | 35.0 |
| Non-ionic wetting agent, e.g. p-nonyl-phenol-ethylene oxide (1:12) adduct | 4.0 |
| Dispersing agent, e.g. sodium salt of maleic acid anhydride/diisobutylene copolymer | 4.0 |
| Tert.butylhydroxytoluene(BHT) | 1.0 |
| Chalk | 16.0 |

EXAMPLE 2

This Example illustrates the preparation of an emulsion concentrate.

|  | g/l |
|---|---|
| Active ingredient of formula I, e.g. as in Example 1 | 250.0 |
| Active ingredient of formula II, e.g. as in Example 1 | 50.0 |
| Non-ionic emulsifier, e.g. oleyl alcohol-ethylene oxide adduct (1:10) | 50.0 |
| Anionic emulsifier, e.g. calcium dodecyl-benzene sulphonate | 25.0 |
| Cyclohexanone | ad 1000 ml |

EXAMPLE 3

This Example illustrates the preparation of a suspension concentrate.

|  | g/l |
|---|---|
| Active substance of formula I, e.g. 4-[3-(p-tert.butyl-phenyl)-2-methyl-propyl]-2,6-dimethyl-morpholine or 1-[3-(p-tert.-butyl-phenyl)-2-methyl-propyl]-piperidine | 320.0 |
| Active substance of formula II, e.g. 1-tert.butyl-2-(1,2,4-triazol-1-yl)-2-(o,p-dichlorobenzyl)-ethanol | 50.0 |
| Non-ionic emulsifier, e.g. oleyl alcohol-ethylene oxide adduct (1:10) | 50.0 |
| Dispersing agent, e.g. polycondensation | 50.0 |

-continued

| | g/l |
|---|---|
| product of phenol and formaldehyde | |
| Anti-settling agent, e.g. sodium alginate | 1.0 |
| Water, deionized | ad 1000 ml |

EXAMPLE 4

The active ingredient combinations were used as follows for the control of the plant fungi:
*Erysiphe graminis* (on spring wheat)
*Puccinia coronata* (on oats)
*Puccinia dispersa* (on rye)
*Puccinia triticina* (on winter wheat)
under practical conditions:

The fungicidal composition was applied after infecting the cereals with the fungi by transplanting diseased young cereal plants in the healthy stock, the application being carried out as soon as about 10–15% of the cereal leaves showed rust disease symptoms or about 15–20% of the cereal leaves showed mildew infestation symptoms. A spray liquor, which was previously prepared in a tank mixing process by adding the individual active substances of formula I and II, mixing with the formulation adjuvants and, if necessary, duluting the initially obtained spray liquor concentrate, was applied to the diseased plants. The amount used was 1000 l/ha. In the case of severe and persistant infestation a further treatment was carried out in each case, namely 2–3 weeks after the first treatment.

3–5 weeks after the (last) treatment the percentage infestation reduction compared with the untreated controls in the stock was determined. The results are compiled in the following Table.

TABLE

| Active substance, g/ha | | % Reduction Fungi/Plants | | | |
|---|---|---|---|---|---|
| Cis-4-[3-(p-tert.butyl-phenyl)-2-methyl-propyl]-2,6-dimethyl-morpholine | 1-Tert.butyl-2-(1,2,4-triazol-1-yl)-2-(o,p-di-chlorobenzyl)-ethanol | Erysiphe graminis/ spring wheat | Puccinia Coronata/ oats | Puccinia dispersa/ rye | Puccinia triticina/ winter wheat |
| 0 | 125 | 94 | 94 | 94 | 94 |
| 750 | 0 | 96 | 98 | 96 | 96 |
| 260 | 40 | 95 | 99 | 96 | 99 |
| 250 | 50 | 96 | 100 | 99 | 99 |
| 350 | 50 | 97 | 99 | 99 | 99 |

I claim:

1. A fungicidal composition comprising an amount, which is effective as a fungicide, of a combination of compound I cis-4-[3-(p-tert.butyl-phenyl)-2-methyl-propyl]-2,6-dimethyl morpholine and compound II 1-tert.butyl-2-(1,2,4-triazol-1-yl)-2-(o,p-dichlorobenzyl)-ethanol, wherein compounds I and II are present in the weight ratio of 2-10:1.

2. The fungicidal composition of claim 1, wherein the weight ratio of 3–9:1.

3. A method for combatting plant fungi, which comprises treating plants to be protected with a fungicidally effective amount of the composition of claim 1.

* * * * *